US008479725B2

(12) United States Patent
Hausmann et al.

(10) Patent No.: US 8,479,725 B2
(45) Date of Patent: Jul. 9, 2013

(54) NEBULISER

(75) Inventors: Matthias Hausmann, Rees (DE); Uwe Hegemann, Herne (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1365 days.

(21) Appl. No.: 11/426,411

(22) Filed: Jun. 26, 2006

(65) Prior Publication Data

US 2007/0029475 A1 Feb. 8, 2007

(30) Foreign Application Priority Data

Jun. 24, 2005 (DE) ......................... 10 2005 029 746

(51) Int. Cl.
*A61M 11/00* (2006.01)
*A61M 15/00* (2006.01)
*A61M 16/00* (2006.01)

(52) U.S. Cl.
USPC ............ 128/200.14; 128/200.24; 128/203.12; 128/203.15

(58) Field of Classification Search
USPC ............... 222/321.6, 325, 386.5, 83.5, 402.1, 222/385, 383.1; 239/338, 339, 302, 321, 239/333, 337, 102.1, 102.2; 128/200.11–200.22, 128/203.12, 203.15, 203.16, 203.17, 203.26, 128/203.27, 204.14, 204.17; 261/DIG. 65, 261/129, 154; 122/4 A, 5.5 A, 7 B, 13.01, 122/13.3–19.2, 33, 487, DIG. 7
See application file for complete search history.

(56) References Cited

U.S. PATENT DOCUMENTS

| | | | | |
|---|---|---|---|---|
| 2,158,318 | A * | 5/1939 | Bernhardt | 222/321.9 |
| 2,213,846 | A * | 9/1940 | Meyer | 239/326 |
| 2,272,943 | A * | 2/1942 | Healy | 239/362 |
| 2,550,840 | A * | 5/1951 | Martin et al. | 222/402.25 |
| 3,248,022 | A * | 4/1966 | Schulman et al. | 222/153.13 |
| 3,272,402 | A * | 9/1966 | Frangos | 222/402.24 |
| 4,251,032 | A * | 2/1981 | Werding | 239/323 |
| 4,885,017 | A * | 12/1989 | Fleischmann | 62/6 |
| 5,322,057 | A * | 6/1994 | Raabe et al. | 128/203.12 |
| 5,497,944 | A * | 3/1996 | Weston et al. | 239/321 |
| 5,640,951 | A * | 6/1997 | Huddart et al. | 128/204.17 |
| 5,662,271 | A | 9/1997 | Weston et al. | |
| 6,195,504 | B1 * | 2/2001 | Horie et al. | 392/394 |
| 6,497,373 | B2 * | 12/2002 | Jaeger et al. | 239/333 |
| 6,726,124 | B2 | 4/2004 | Jaeger et al. | |
| 6,802,461 | B2 * | 10/2004 | Schneider | 239/337 |
| 6,918,547 | B2 | 7/2005 | Jaeger et al. | |

FOREIGN PATENT DOCUMENTS

| | | | |
|---|---|---|---|
| WO | 9114468 | A1 | 10/1991 |
| WO | 9712687 | A1 | 4/1997 |
| WO | 0132247 | A1 | 5/2001 |

* cited by examiner

*Primary Examiner* — Annette Dixon
(74) *Attorney, Agent, or Firm* — Roberts Mlotkowski Safran & Cole, P.C.; David S. Safran

(57) ABSTRACT

A nebulizer for a fluid which has a conveying tube for conveying fluid and a method for producing a thick-walled capillary. The conveying tube or the capillary is of multipart and/or double-walled construction, and in particular, is made up of a number of parts, such as an inner tube and an outer tube. This construction allows the device to be manufactured more easily and cheaply, in particular, when the inner diameters are very small.

37 Claims, 8 Drawing Sheets

NEBULISER

BACKGROUND OF THE INVENTION

1. Field of the Invention

The present invention relates to a nebuliser for a fluid having a conveying tube for conveying the fluid, wherein in particular the conveying tubeis constructed as a thick-walled capillary and a method of producing a thick-walled capillary.

2. Description of Related Art

A nebuliser available under the trademark RESPIMAT® in the form of an inhaler is known, and is illustrated in its basic form in International Patent Application Publication WO 91/14468 A1 (U.S. Pat. No. 5,662,271) and in a specific configuration in International Patent Application Publication WO 97/12687 A1 (U.S. Pat. Nos. 6,918,547 and 6,726,124) as well as in FIGS. 1 & 2 of the accompanying drawings of this application. The nebuliser has a conveyor device with a conveying tube for conveying and atomising the fluid. The conveying tube is constructed, in particular, as a thick-walled massive capillary, as shown in FIG. 3*b* of WO 97/12687 A1. The conveying tube is therefore very difficult and complex to produce.

Capillaries with a small internal diameter and thin walls are generally obtainable. Capillaries with a thick wall and small manufacturing tolerances are, however, very difficult to produce and often have undesirably rough inner walls. This can be explained by the many forming steps (which are often, in the last analysis, carried out without a core because of the small internal diameter), needed to produce a thick-walled massive capillary.

In the present application the term "capillary" relates, in particular, to microfluidic, preferably, elongate structures with a hydraulic diameter of less than 1000 μm, particularly, preferably, less than 500 μm. The internal cross-section is preferably, but not necessarily, at least essentially round. The same is true, in particular, of the outer contour of the preferably, tubular or cylindrical capillary. However, the capillary may also have other non-round internal and/or external cross-sections or contours.

The term "thick-walled" refers herein to a capillary, particularly, when the mean inner diameter is less than 50% of the outer diameter, particularly, less than 30%, and/or when the wall thickness is more than 0.3 mm, preferably, more than 0.5 mm.

SUMMARY OF THE INVENTION

A primary object of the present invention is to provide a nebuliser having a conveying tube and a method of producing a capillary, wherein the conveying tube or the capillary is simple and inexpensive to produce with a thick-walled construction, and particularly, with a smooth inner wall, while having great stability.

This aim is achieved by a nebuliser and method according to one aspect of the present invention by making a thick-walled capillary or a conveying tube of a nebuliser preferably, formed therefrom with a double-walled construction. This enables the object to be produced more easily and hence more cheaply than in the prior art, with low manufacturing tolerances. In particular, it is possible to achieve a smoother inner surface. The double-walled construction, in fact, makes it possible to use standard commercial thin-walled capillaries, so that the large number of forming steps that were previously required can be eliminated or reduced.

Particularly, preferably, an inner tube is concentrically installed in an outer tube to form the conveying tube or the thick-walled capillary. The tubes are then constructed, in particular, as thin-walled capillaries which can be obtained cheaply and to a high quality.

The proposed thick-walled capillary is preferably, used as a conveying tube in a proposed nebuliser. The following discussion will therefore be directed primarily to the use of the capillary as a conveying element or conveying tube for a fluid which is to be nebulised in a nebuliser of this kind. However, the thick-walled capillary may also be used for other purposes. This also applies to the method described for producing the conveying tube or the thick-walled capillary.

Further advantages, features, properties and aspects of the present invention will become apparent from the following description of preferred embodiments with reference to the accompanying drawings.

DETAILED DESCRIPTION OF THE INVENTION

Figure 1:
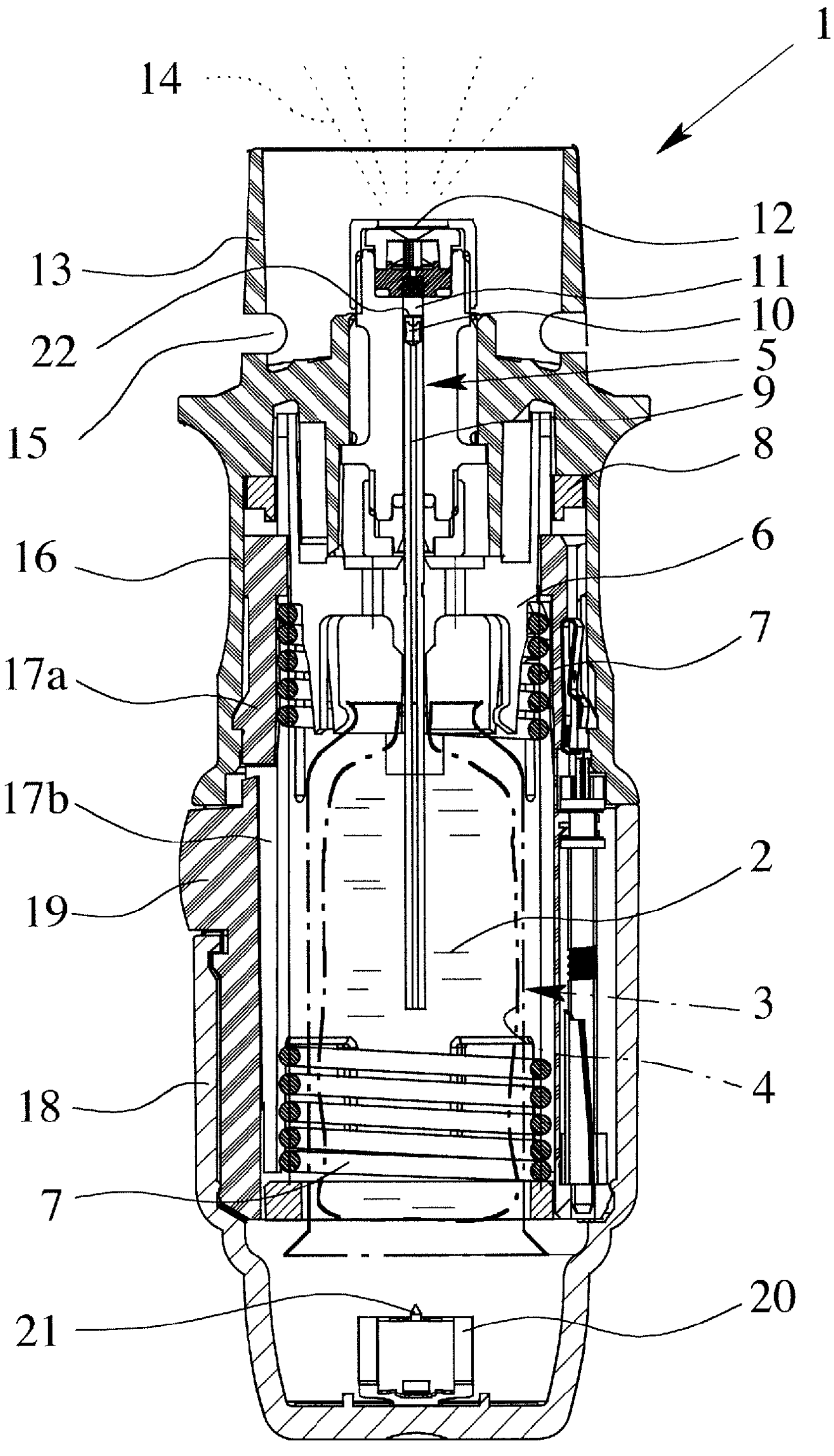
FIG. 1 is a schematic section through a known nebuliser in an untensioned state.

In the figures, the same reference numerals have been used for identical or similar parts, resulting in corresponding or comparable properties and advantages, even if the associated description is not repeated.

Figure 2:
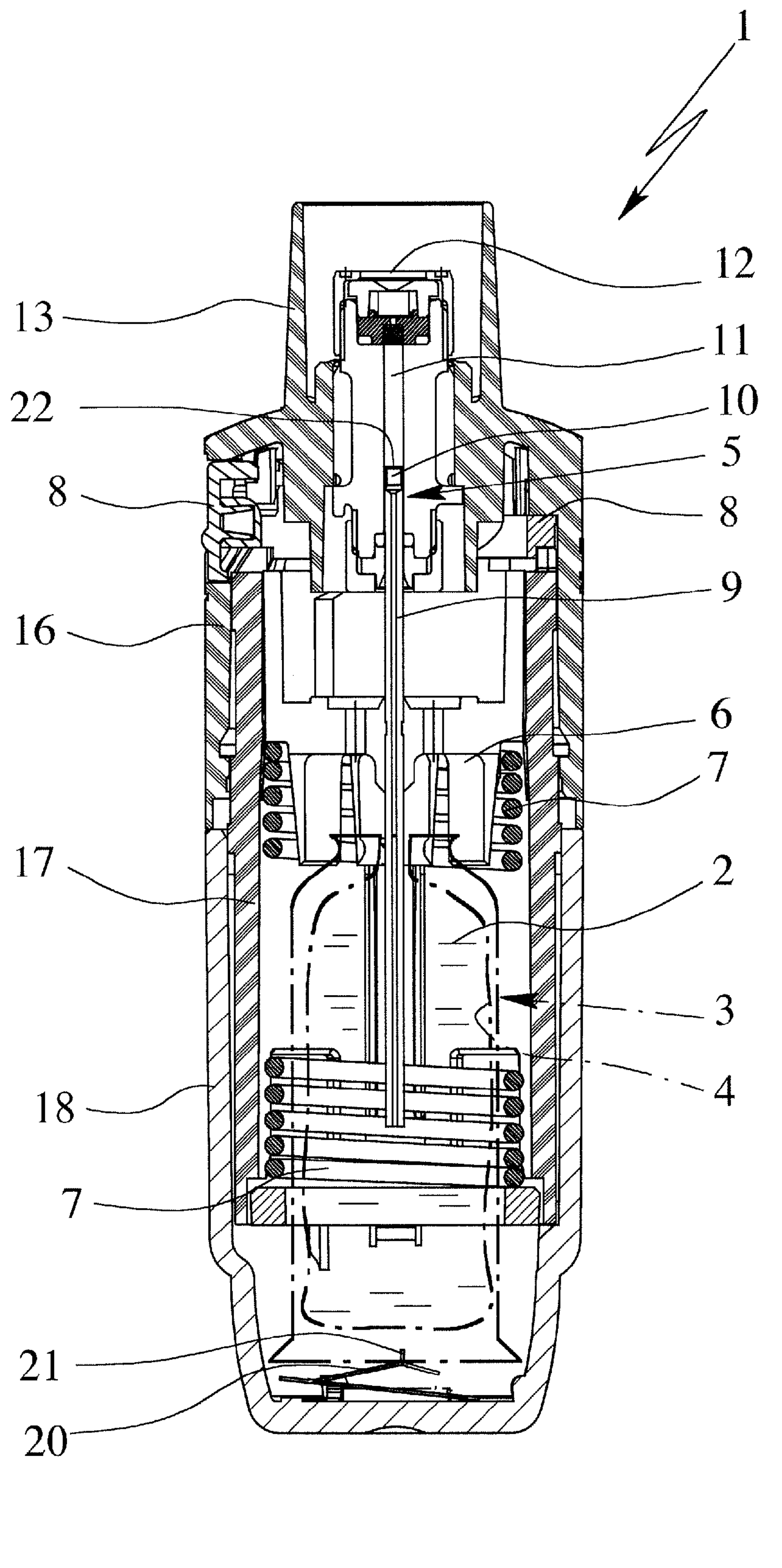
FIG. 2 is a schematic section through the known nebuliser in the tensioned state, rotated 90° as compared with the view of FIG. 1.

FIGS. 1 & 2 show a known nebuliser 1 for atomising a fluid 2, particularly, a highly effective pharmaceutical composition or the like, diagrammatically shown in the untensioned state (FIG. 1) and in the tensioned state (FIG. 2). The nebuliser 1 is constructed, in particular, as a portable inhaler, and preferably, operates without propellant gas.

When the fluid 2, preferably, a liquid, more particularly, a pharmaceutical composition, is nebulised, an aerosol is formed, which can be breathed in or inhaled by a user (not shown). Usually the inhaling is done at least once a day, more particularly, several times a day, preferably, at set intervals, depending on the complaint from which the patient is suffering.

The known nebuliser 1 has an insertable, and preferably, exchangeable container 3 which holds the fluid 2. The container thus forms a reservoir for the fluid 2 which is to be nebulised. Preferably, the container 3 contains an amount of fluid 2 or active substance which is sufficient to provide up to 200 dosage units, for example, i.e., to allow up to 200 sprays or applications.

The container 3 is substantially cylindrical or cartridge-shaped and once the nebuliser 1 has been opened, the container can be inserted therein from below and changed if desired. The container 3 is of rigid construction, the fluid 2, preferably, being held in a fluid chamber 4 that is in the form of a collapsible bag in the container 3.

The nebuliser 1 also has a conveying device, particularly, a pressure generator 5 for conveying and nebulising the fluid 2, particularly, in a preset and optionally adjustable dosage amount.

The nebuliser 1 or pressure generator 5 has a holder 6 for the container 3, an associated drive spring 7 being only partly shown, a locking element 8 which can be manually operated to release it, a conveying tube 9 that is, preferably, in the form of a thick-walled capillary, with an optional valve, particularly, a non-return valve 10, a pressure chamber 11 and/or an expulsion nozzle 12 in the region of a mouthpiece 13. The container 3 is fixed in the nebuliser 1 via the holder 6, particularly, by locking engagement, such that the conveying tube 9 penetrates into the container 3. The holder 6 may be constructed so that the container 3 can be detached and exchanged.

As the drive spring 7 is axially tensioned, the holder 6 with the container 3 and the conveying tube 9 is moved downwards in the drawings and fluid 2 is sucked out of the container 3 through the non-return valve 10 into the pressure chamber 11 of the pressure generator 5.

During the subsequent relaxation after actuation of the locking element 8, the fluid 2 in the pressure chamber 11 is put under pressure as the conveying tube 9, with its now closed non-return valve 10, is moved back upwards by the relaxation of the drive spring 7 and now acts as a pressing ram. This pressure forces the fluid 2 through the expulsion nozzle 12, whereupon it is nebulised into an aerosol 14, as shown in FIG. 1.

A user or patient (not shown) can inhale the aerosol 14, while an air supply can be sucked into the mouthpiece 13 through at least one air supply opening 15.

The nebuliser 1 comprises an upper housing part 16 and an inner part 17 which is rotatable relative thereto (FIG. 2) having an upper part 17*a* and a lower part 17*b* (FIG. 1), while an, in particular, manually operable housing part 18 is releasably fixed, particularly, fitted onto the inner part 17, preferably, by means of a retaining element 19. In order to insert and/or replace the container 3, the housing part 18 can be detached from the nebuliser 1.

The housing part 18 can be rotated relative to the upper housing part 16, carrying with it the part 17*b* of the inner part 17 which is lower down in the drawings. As a result, the drive spring 7 is tensioned in the axial direction by means of a gear (not shown) acting on the holder 6. During tensioning, the container 3 is moved axially downwards until the container 3 assumes an end position as shown in FIG. 2. In this state, the drive spring 7 is under tension. When the tensioning is carried out for the first time, an axially acting spring 20 disposed in the housing part 18 comes to abut on the base of the container and by means of a piercing element 21 pierces the container 3 or a seal at the bottom when it first comes into abutment therewith, for venting. During the nebulising process, the container 3 is moved back into its original position shown in FIG. 1 by the drive spring 7, while the conveying tube 9 is moved with its outlet end 22 into the pressure chamber 11. The container 3 and the conveying element or conveying tube 9, thus, execute a lifting movement during the tensioning process or for drawing up the fluid and during the atomising process.

The construction and mode of operation of several embodiments of a proposed nebuliser 1 and method will now be described in more detail, referring to the other figures, which are not to scale, but emphasising only the essential differences from the nebuliser 1 according to FIGS. 1 & 2. The remarks relating to FIGS. 1 & 2 thus apply accordingly or in a supplementary capacity, while any desired combinations of features of the nebuliser 1 according to FIGS. 1 & 2 and the nebuliser 1 according to the embodiments described below or with one another are possible.

Figure 3:
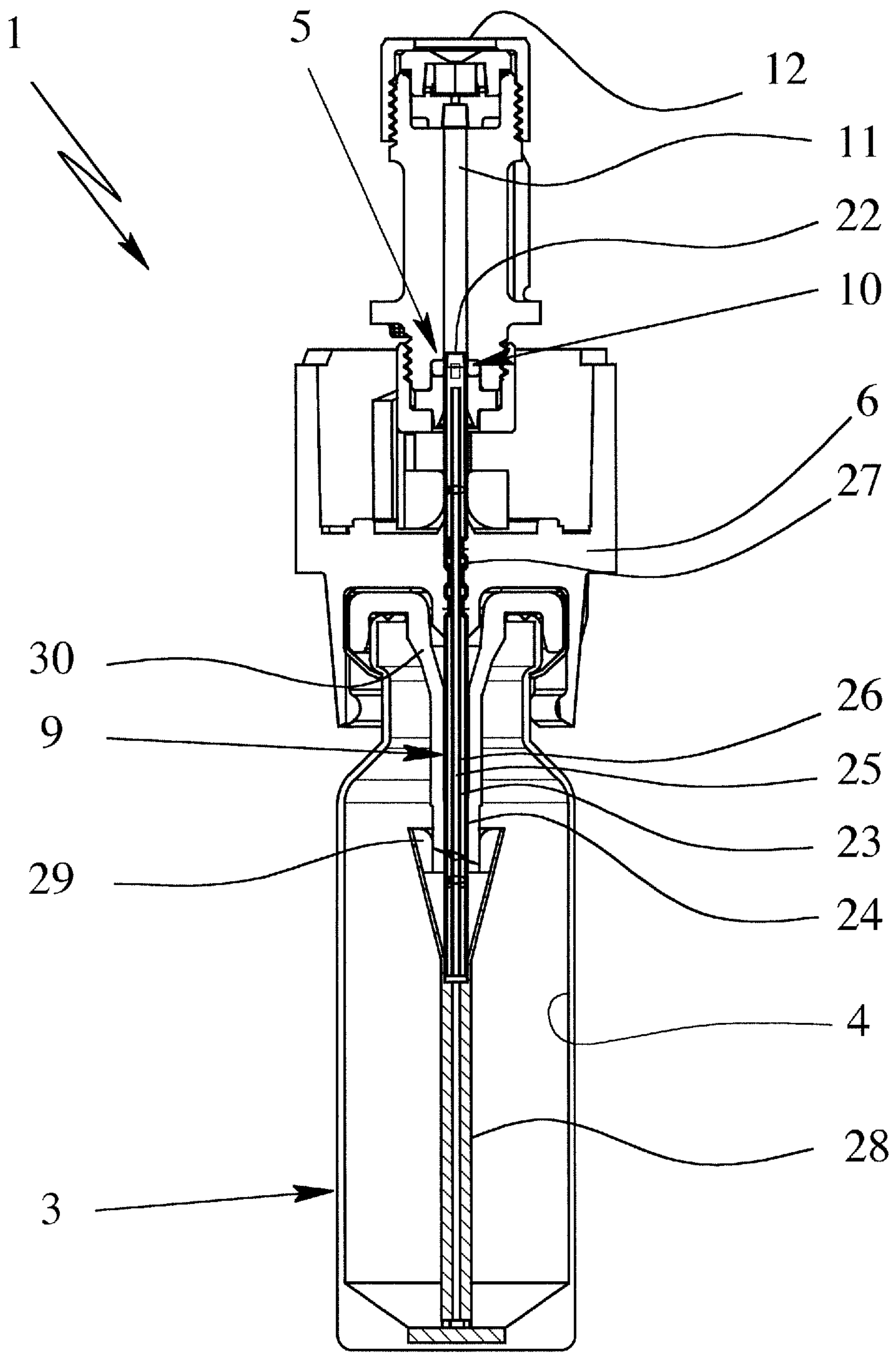
FIG. 3 is a schematic section, not to scale, through a proposed nebuliser with a conveying tube according to a first embodiment.

FIG. 3 shows, in schematic section, the container 3 and part of the associated proposed nebuliser 1 according to a first embodiment. The conveying tube 9 comprises an inner tube 23 and an outer tube 24, which are preferably, arranged concentrically to one another and/or formed as thin walled, in particular standard commercial capillaries.

The conveying tube 9 is thus double walled and preferably, multi-part in construction and especially is in the form of a thick walled but preferably, not massive capillary. The double walled and particularly, multi-part construction makes it possible in particular to manufacture the conveying tube 9 particularly, cheaply and/or precisely, most preferably, with a smooth and/or round inner wall or contour.

The inner tube 23 forms a conveying channel 25 on the inside. The annular space 26 between the inner tube 23 and the outer tube 24 preferably, forms a venting channel in the first embodiment. Alternatively, the annular chamber 26 may also preferably, be sealed off in gas tight manner. The two tubes 23 and 24 are preferably, firmly joined together by welding, e.g. in the region of their ends. However, the two tubes 23, 24 may also be joined together by some other method, for example by adhesive bonding, soldering, deformation or the like.

The multi-part construction of the conveying tube 9—either from the two tubes 23 and 24, as explained above, or from even more parts—if necessary, may also be used independently of any venting, in particular, in a nebuliser 1 of the type described hereinbefore or some other nebuliser 1. In particular the venting channel in the conveying tube 9 may be omitted or, as already mentioned, sealed off.

In the first embodiment, the conveying tube 9 is preferably, fixedly attached to the holder 6. In particular, the conveying tube 9 or its outer tube 24 is provided for this purpose with a retaining region 27—preferably, having a corrugated outer contour or the like. The conveying tube 9 is preferably, injection molded with the holder 6 at the retaining region 27. Thus, the holder 6, preferably, in the retaining region 27 or thereon engages by interlocking engagement. As a result, the conveying tube 9 is axially secured in the holder 6 by interlocking engagement.

The conveying tube 9 or the thick walled capillary, preferably, has an at least substantially smooth or cylindrical outer wall which is optionally only interrupted by the retaining region 27 which is relatively short in relation to the overall length, in particular.

In the first embodiment, an immersion tube 28, in particular, adjoins the conveying tube 9 and extends, preferably, to the base inside the container 3. In the embodiment shown, the immersion tube 28 is connected to a closure 30 of the container 3, in particular, via a retaining portion 29 which widens out in a funnel shape, so that the conveying tube 9 on insertion into the container 3 or when the closure 30 is pierced, can be inserted into the position shown in the retaining portion 29 of the immersion tube 28 and a fluidic connection is established between the conveying channel 25 and the immersion tube 28.

However, the immersion tube 28 is only optional. As an alternative, this may also be omitted. The conveying tube 9 then extends preferably, up to or into the region of the bottom of the container 3 or fluid chamber 4.

The conveying tube 9 is used, in particular, as a piston for pumping the fluid 2 in the nebuliser 1 or in the conveying device or pressure generator 5. The conveying tube 9 should have a relatively large outer diameter. By contrast, the inner diameter of the conveying tube 9 i.e., the inner diameter of the inner tube 23 or the diameter of the conveying channel 25 thus formed—should be relatively small in order to achieve a small dead volume. Accordingly, it is necessary or at least desirable for the conveying tube 9 to be fairly thick-walled—particularly, in the sense described hereinbefore, and in the first embodiment, this is achieved by concentrically arranging the inner tube 23 inside the outer tube 24. In order to achieve the desired pumping action and/or ensure defined volumes or avoid dead spaces, the annular space 26 between the inner tube 23 and outer tube 24 is preferably, closed off at least at the delivery end, particularly, in fluid tight manner and most particularly, preferably, in gas tight manner as well.

The conveying tube 9 preferably, comprises the valve, particularly, the non-return valve 10 which, in the embodiment shown, is disposed at the downstream end of the conveying tube 9 or at the end which extends into the pressure chamber 11.

The conveying tube 9 or the thick-walled capillary, preferably, is formed at least essentially or totally of metal, particularly, stainless steel, most preferably, austenitic chrome nickel steel. Preferably, at least the inner tube 23 and the outer tube 24 are made of the same material, particularly, metal or stainless steel, as mentioned previously.

The conveying tube 9 or the thick-walled capillary preferably, has an outer diameter (of the outer tube 24) of 1-2 mm and/or an inner diameter (of the inner tube 23) of 0.1-0.6 mm. Preferably, the outer diameter is at least twice or three times as great as the inner diameter. The wall thicknesses of the tubes 23, 24 are preferably, about 0.1 mm or less.

The conveying tube 9 or the thick-walled capillary preferably, has a wall thickness (radial spacing of the inner wall of the inner tube 23 from the outer wall of the outer tube 24) of at least 0.3 mm, most preferably, around 0.5 mm or more.

The proposed thick-walled or double-walled construction of the conveying tube 9 goes beyond the preferred high displacement during its use as a piston and independently thereof leads to a particularly, high stability of the conveying tube 9, which is necessary for example in order to allow safe and definite piercing or other type of opening of the container 3 or the like. However, this stability may also be advantageous in other uses.

Further embodiments of the nebuliser 1 or conveying tube 9 or the thick-walled capillary and the preferred production of the conveying tube 9 or the thick-walled capillary are described hereinafter with reference to the other figures, while only essential difference from the first embodiment are particularly, explained. The previous embodiments therefore apply in a corresponding or supplementary capacity.

Figure 4:
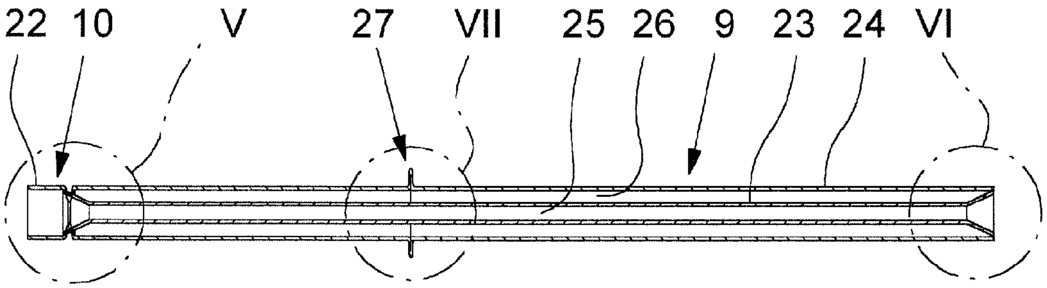
FIG. 4 is a schematic section through a conveying tube according to a second embodiment.

FIG. 4 shows a second embodiment of the conveying tube 9 in section. As in the first embodiment, the conveying tube 9 is, preferably, made in two parts, namely the inner tube 23 and the outer tube 24. Preferably, the two tubes 23, 24 are welded together. The annular space 26 between the tubes 23, 24 is preferably, closed off at both ends, particularly, in gas tight manner.

Figure 5:
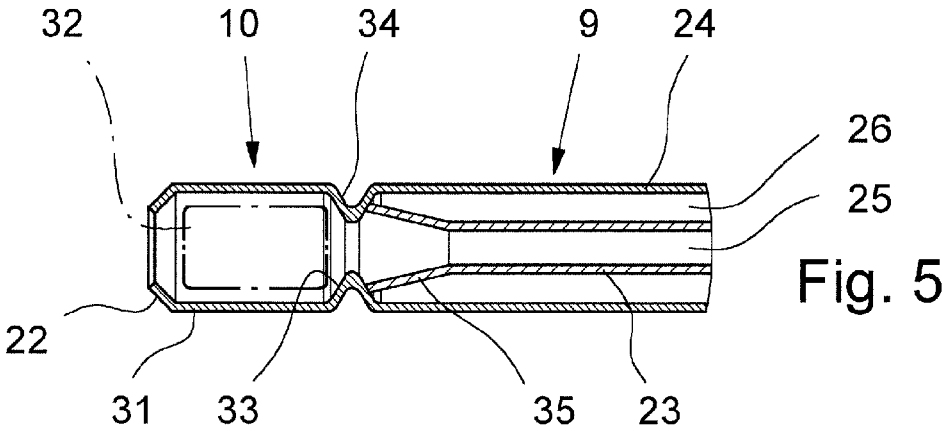
FIG. 5 is an enlarged view of the encircled detail V in FIG. 4.

FIG. 5 shows, in an enlarged detail from FIG. 4, the valve or outlet end 22 of the conveying tube 9. The valve, particularly, a non-return valve 10, is preferably, formed on or by the conveying tube 9 or integrated therein, as in the first embodiment. In the second embodiment the outer tube 24—as in the first embodiment—preferably, forms a valve region 31 extending axially beyond the end of the inner tube 23, in particular, in which a valve member 32 of the valve 10 is accommodated. The valve member 32 is preferably, axially movable. The preferably, inwardly crimped or otherwise deformed end 22 of the outer tube 24 or some other retaining means form an axial stop for the valve member 32 in the outer tube 24 or valve region 31 and delimit the axial mobility of the valve member 32 accordingly.

The conveying tube 9 also preferably, forms a valve seat 33 for the valve 10 for the valve body 32. The valve body 32, preferably, sits axially on the valve seat 33 when the valve 10 is closed, i.e., during the nebulising process.

In the second embodiment, the valve seat 33 is, preferably, formed by a concentric region or section of the outer tube 24, particularly, an encircling narrowing or bead 34. However, other constructive solutions are also possible.

The inner tube 23 preferably, has a radially widening, particularly, at least partially conical connecting portion 35 which, in this case, is formed at the end of the inner tube 23 and expands, in particular, at least substantially to the inner diameter of the outer tube 24. The two tubes 23, 24 are joined together by the connecting portion 35, particularly, by welding, gluing or the like. For example, it is possible to carry out welding through the outer wall of the outer tube 24 in a substantially radial direction.

Thus, the inner tube 23 extends at least substantially as far as the valve seat 33 or up to the preferably, radial narrowing or bead 34, thus minimising the volume through which the fluid 2 can flow in the conveying tube 9 or conveying channel 25.

Figure 6:
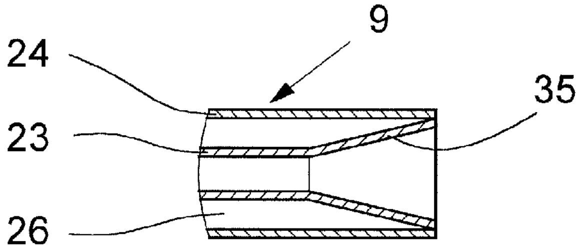
FIG. 6 is an enlarged view of the encircled detail VI in FIG. 4.

FIG. 6 shows, in an enlarged detail from FIG. 4, the other end of the conveying tube 9. Here again, the inner tube 23 is, preferably, connected to the outer tube 24 via a connecting portion 35 which widens out radially, in particular. In the embodiment shown, the inner tube 23 or its connecting portion 35, preferably, terminates flush with the axial end of the outer tube 24 and is axially welded to the outer tube 24 in this region, in particular.

In the second embodiment, the inner tube 23, is preferably, attached, particularly, by welding, to the outer tube 24 at its two ends. However, the inner tube 23 may also be radially connected to the outer tube 24 by spacers or other means between its two ends or may be at least radially held or guided.

In the second embodiment, the annular space 26 (axial interstice between the inner tube 23 and the outer tube 24) is preferably, hermetically sealed, particularly, in fluid tight and gas tight manner.

In the second embodiment, the annular space 26 is preferably, of hollow construction, i.e. it is not filled with a medium, only air. However, while this is theoretically possible, the interstice 26 may be at least partly filled with an adhesive, an insulating material or some other suitable material.

In the second embodiment, the conveying tube 9 or outer tube 24, preferably, has an outer diameter that remains at least substantially constant over its entire length. If required, the outer diameter of the valve region 10 may also be reduced. The retaining region 27 may, optionally, project radially relative to the above mentioned outer diameter, as explained below.

Figure 7:
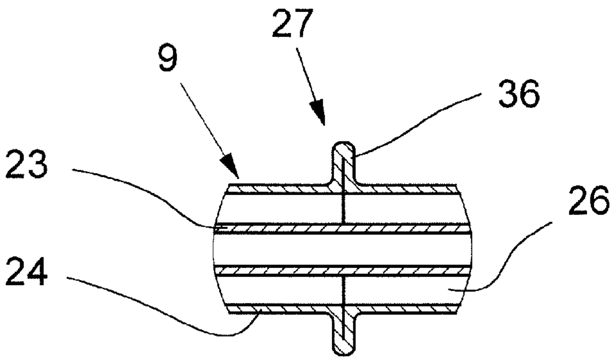
FIG. 7 is an enlarged view of the encircled detail VII in FIG. 4.

FIG. 7 shows, in an enlarged detail from FIG. 4, the retaining region 27 of the conveying tube 9. The retaining region 27 is formed in the second embodiment by an external radial projection 36, particularly, in the form of a flange-like crimped edge. The projection 36 or crimped edge projects radially outwards relative to the outer diameter of the conveying tube 9 or outer tube 24. The retaining region 27 preferably, serves to secure the conveying tube 9 in the holder 6 by interlocking engagement in the axial direction (see, FIG. 3).

Figure 8:
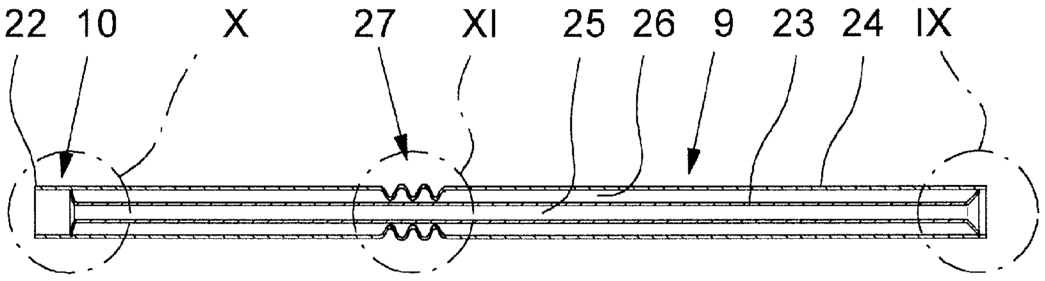
FIG. 8 is a schematic section, not to scale, through a conveying tube according to a third embodiment.

FIG. 8 shows a, third embodiment of the conveying tube 9 in section. The fourth embodiment is very similar to the second embodiment, and consequently, only the major differences will be described below.

The conveying tube 9 is preferably, once again made in only two parts, namely the inner tube 23 and the outer tube 24.

Figure 9:
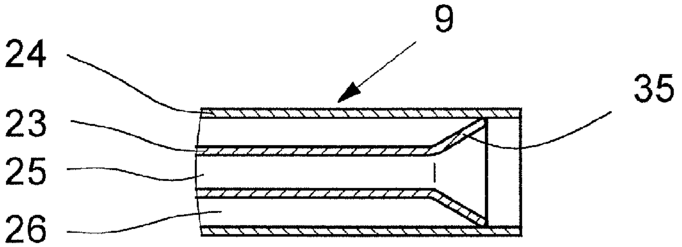
FIG. 9 is an enlarged view of the encircled detail IX in FIG. 8.

FIG. 9 shows, in an enlarged detail from FIG. 8, the inflow end of the conveying tube 9. The inner tube 23 is preferably, set back, with its connecting portion 35, relative to the end of the outer tube 24. This makes it easier to adhere to the length tolerance of the conveying tube 9.

Figure 10:
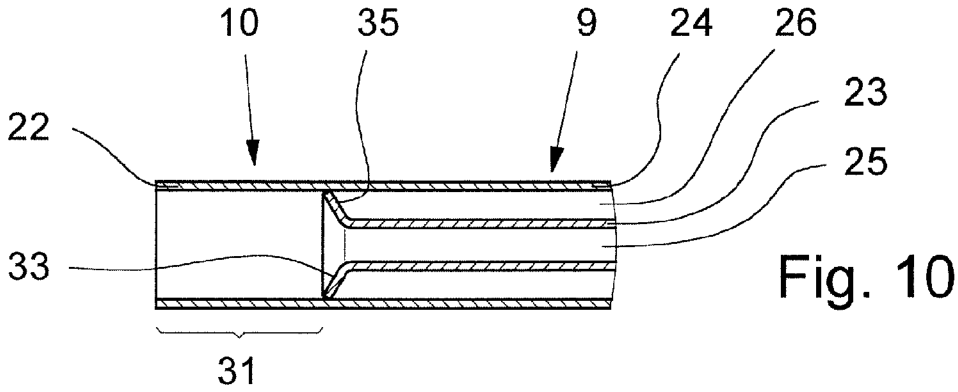
FIG. 10 is an enlarged view of the encircled detail X in FIG. 8.

FIG. 10 shows in an enlarged detail from FIG. 8, the valve end 22 of the conveying tube 9 (without terminal crimping and without a valve member 32). The valve seat 33 is formed here by the axially expanding connecting portion 35 of the inner tube 23 at this end. Accordingly, in this embodiment, the outer tube 24 preferably, does not have any narrowing or bead 34 in this area.

Figure 11:
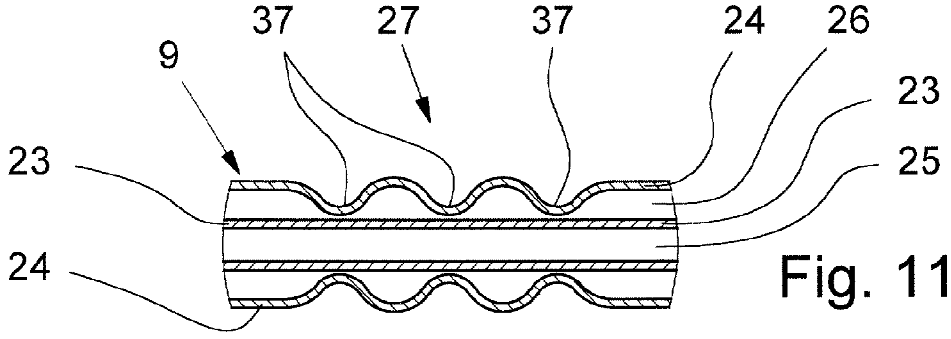
FIG. 11 is an enlarged view of the encircled detail XI in FIG. 8.

FIG. 11 shows, in an enlarged detail from FIG. 8, the retaining region 27 of the conveying tube 9. Instead of a projection, the retaining region 27, in this fourth embodiment, preferably, has a radial indentation or recess 37 particularly, an annual groove, a step, a bead or the like, several of which may be provided one behind the other and in particular a corrugated outer contour may be formed by the retaining region 27.

According to a particularly, preferred aspect, the outer tube 24 at the retaining region 27 is deformed axially inwards such that it bears on the inner tube 23. If necessary, the outer tube 24 in this contact region may also be fixedly connected to the inner tube 23, e.g., by welding or adhesive bonding. This can contribute to the overall stability of the conveying tube 9. However, it is also possible for a radial spacing to be maintained between the outer tube 24 and the inner tube 23 at the retaining region 27.

Figure 12:
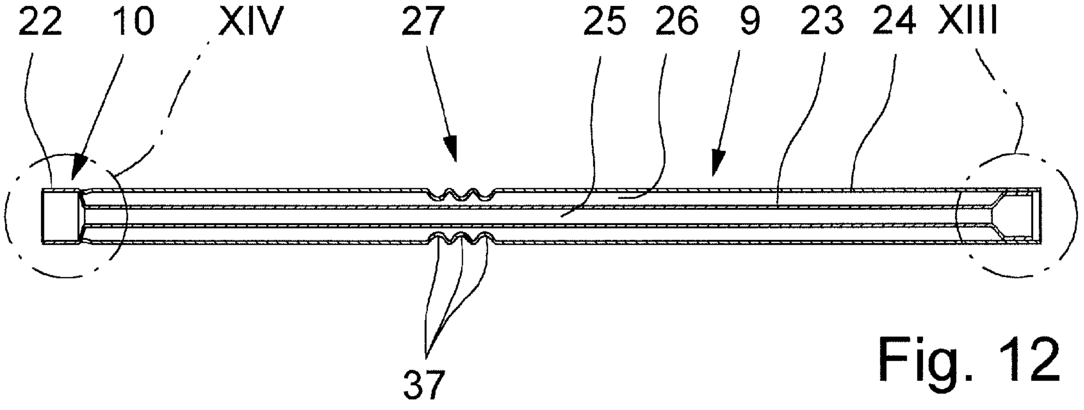
FIG. 12 is a schematic section, not to scale, through a conveying tube according to a fourth embodiment.

FIG. 12 shows a fourth embodiment of the conveying tube 9 in section. The fourth embodiment is very similar to the second and third embodiments. In particular, the conveying tube 9, according to the fourth embodiment, is again made in only two parts, preferably, the inner tube 23 and outer tube 24.

Figure 13:
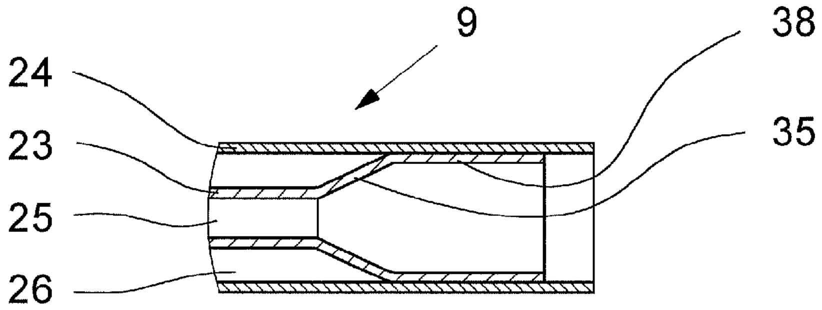
FIG. 13 is an enlarged view of the encircled detail XIII in FIG. 12.

FIG. 13 shows, in an enlarged detail from FIG. 12, the inflow end of the conveying tube 9. The inner tube 23 or its connecting portion 35 in the fourth embodiment has a cylindrical portion 38 which adjoins the conical or radially expanding portion of the connecting portion 35 and has an outer diameter which corresponds at least substantially to the inner diameter of the outer tube 24. The inner tube 23 is preferably, connected in fluid tight and more preferably, gas tight manner to the outer tube 23 via the cylindrical portion 38, e.g., by welding, gluing, or the like.

The cylindrical portion 38 or the inner tube 23 is also preferably, recessed inwardly or set back relative to the associated end of the outer tube 24 in the fourth embodiment as well.

Figure 14:
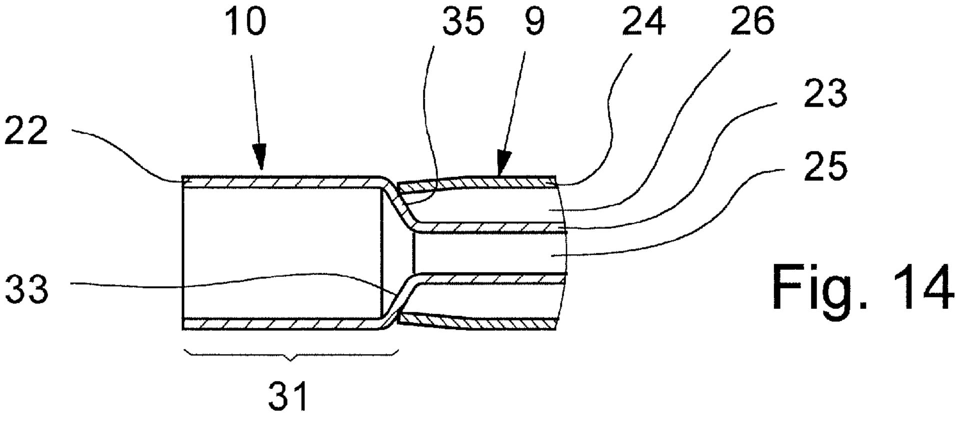
FIG. 14 is an enlarged view of the encircled detail XIV in FIG. 12.

FIG. 14 shows, in an enlarged detail from FIG. 12, the outflow or valve end 22 of the conveying tube 9 (without terminal crimping and without a valve member 32). In the fourth embodiment, the inner tube 23, preferably, forms the valve region 31 of the valve 10. In particular, the preferably, at least substantially hollow cylindrical valve region 31 is directly adjacent to the conical connecting portion 35 of the inner tube 23 which forms the valve seat 33.

Preferably, the receiving region 31 has an outer diameter which corresponds to the outer diameter of the outer tube 24. In this case the outer tube 24 preferably, terminates at the connecting portion 35 of the inner tube 23 and does not extend as far as the valve end of the conveying tube 9, as shown in FIG. 14. If necessary the outer tube 24 may taper conically in its end region to make it easier to connect it to the inner tube 23, e.g., by welding.

Figure 15:
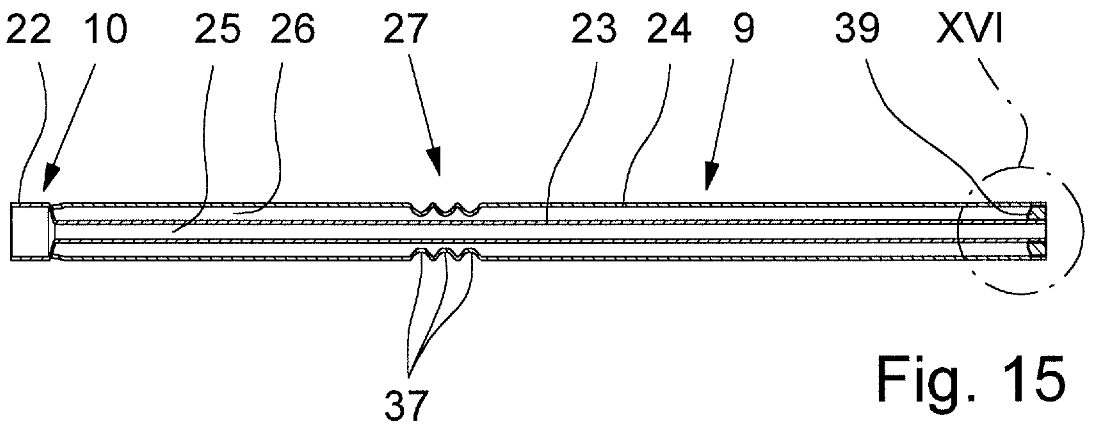
FIG. 15 is a schematic section, not to scale, through a conveying tube according to a fifth embodiment.
Figure 16:
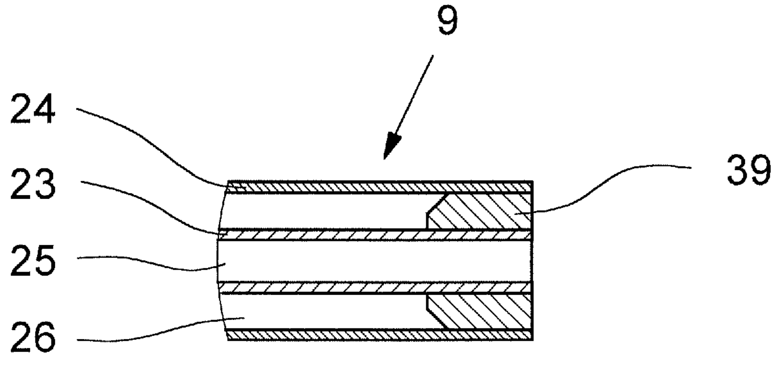
FIG. 16 is an enlarged view of the encircled detail XVI in FIG. 15.

FIG. 15 shows a fifth embodiment of the conveying tube 9 in section. The fifth embodiment corresponds substantially to the fourth embodiment. The only difference is that at the inflow end the inner tube 23 is preferably, connected via a separate spacer element 39 to the outer tube 24, as indicated in FIG. 19, which shows an enlarged detail from FIG. 18. The spacer element 39 is, preferably, at least substantially hollow cylindrical or sleeve-shaped or annular in construction and closes off the annular space 26 axially or at its end face. In particular, the radially widening connecting portion 35 on the inner tube 23 at the inflow end can be omitted. The two tubes 23, 24, preferably, terminate together with the spacer element 39 in an end plane or axial plane and are preferably, axially welded thereto. However, the spacer element 39 may also be pressed in or on, attached by gluing or by some other method.

The spacer element 39, preferably, has a wall thickness of at least substantially 50% of the difference between the inner diameter 24 and the outer diameter of the inner tube 23. The spacer element 39 is located, in particular, in a snug fit or press fit.

The spacer element 39, preferably, has a length of less than 20%, particularly, preferably, less than 10%, of the total length of the conveying tube 9. Alternatively, the spacer element 39 may also extend over a substantially greater length, in particular, to increase the kink resistance of the conveying tube 9. For example, the spacer element 39 may even extend as far as the retaining region 28 or to the indentation or bead 34.

In the fifth embodiment, the conveying tube 9 is no longer made in two parts but preferably, in three parts. In spite of the greater number of parts, manufacture is simpler since the individual components can be manufactured very simply, inexpensively and with great precision.

Figure 17:
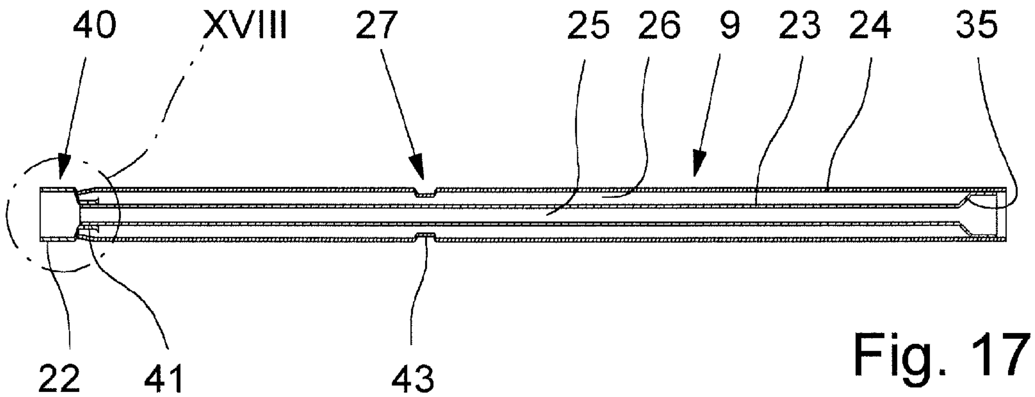
FIG. 17 is a schematic section, not to scale, through a conveying tube according to a sixth embodiment.

FIG. 17 shows a sixth embodiment of the conveying tube 9 in section. The seventh embodiment is very similar to the fifth embodiment. However, instead of two parts, the conveying tube 9, here, is made up of three parts. The retaining region 27 is, preferably, in the form of an encircling annular groove or depression.

Figure 18:
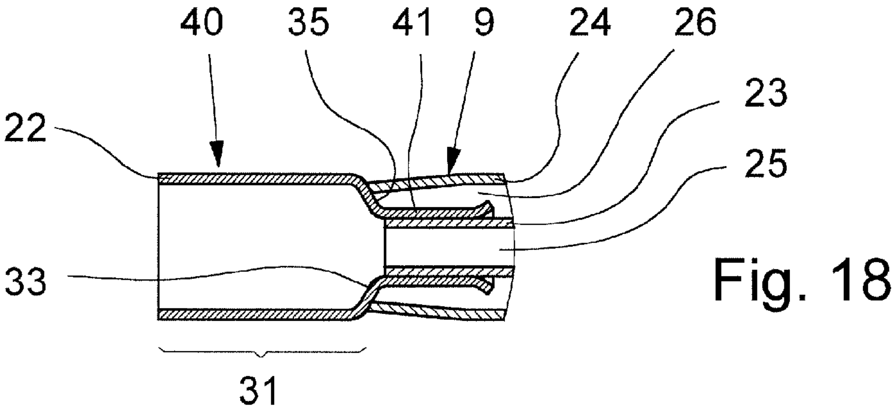
FIG. 18 is an enlarged view of the encircled detail XVIII in FIG. 17.
Figure 19:
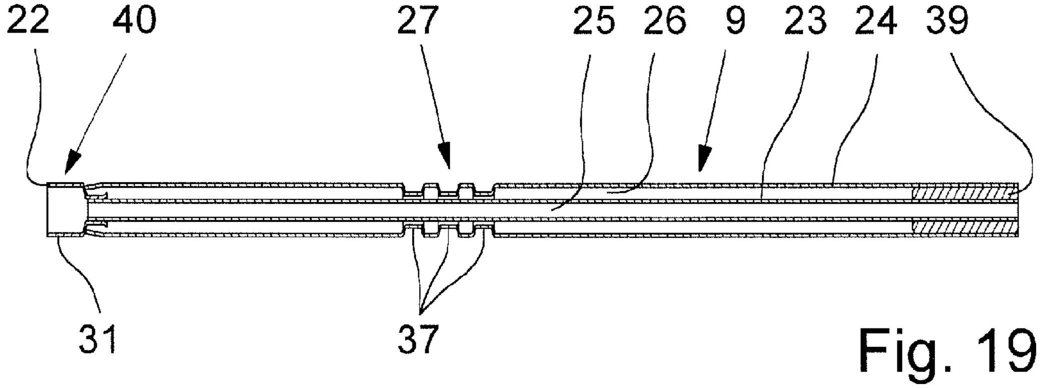
FIG. 19 is a schematic section, not to scale, through a conveying tube according to a seventh embodiment.

FIG. 18 shows, in an enlarged detail from FIG. 17, the valve end 22 of the conveying tube 9. The conveying tube 9 in the sixth embodiment, preferably, has a valve member or connecting member 40 which is produced separately from the inner tube 23 and outer tube 24, and which forms the receiving region 31 of the valve 10 and/or connects the two tubes 23, 24.

The valve member or connecting member 40 has, in particular a, preferably, conical connecting portion 35 adjoining the receiving region 31, which connects the two tubes 23, 24 and/or again forms the valve seat 33.

The outer tube 24 and the receiving region 31 of the valve member or connecting member 40, preferably, in turn, have at least substantially the same outer diameter as in the third and fourth embodiments. The outer tube 24, preferably, terminates at the connecting portion 35 of the valve member or connecting member 40, as indicated in FIG. 18, where the outer tube 24 is tightly joined to the connecting member 27, in particular by welding. If necessary the end part of the outer tube 24 may in turn be conically tapered.

With a correspondingly reduced diameter, preferably, an at least substantially hollow cylindrical or sleeve-shaped connecting region 41 adjoins the connecting portion 35 and is pushed or fitted or pressed onto the inner tube 23 and attached thereto, particularly, by welding. In particular, the valve member or connecting member 40 is constructed as a deep-drawn part which is relatively easy to produce.

FIG. 19 shows a seventh particularly, preferred embodiment of the conveying tube 9 in section. Here, the conveying tube 9 is, preferably, made up of at least four parts, namely, the inner tube 23, the outer tube 24, the spacer element 39 and the valve member or connecting member 40. At the inflow end, the two tubes 23, 24, preferably, are connected by means of the spacer element 39, in particular, as in the sixth embodiment.

At the outlet or valve end 22, the two tubes 23, 24, preferably, are joined together by the valve member or connecting member 40 as in the seventh embodiment.

In spite of the multiplicity of parts, namely at least four components, the seventh embodiment is relatively simple and cheap to produce, particularly, with low manufacturing tolerances and if necessary with a very smooth and even inner wall.

Initially, the valve member or connecting member 40 and the inner tube 23 are joined together, particularly, by welding. It is particularly, preferable for the welding to be carried out radially from outside in the connecting region 41. In this way a first assembly is formed.

In addition, the outer tube 24 and the spacer element 39 are joined together, particularly, by welding, to form a second assembly. The welding is preferably, carried out at the end face or at the inlet end.

Then, the two assemblies are combined and firmly joined together. In particular, the outer tube 24 is welded to the valve member or connecting member 40. This may be done essentially radially. Moreover, the spacer element 39 is fixedly connected to the inner tube 23, in particular axially welded thereto.

If the conveying tube 9 is provided with the optional valve 10, as in the embodiment shown, the valve member 32 (not shown) is then introduced into the valve region 10 and secured, preferably, by final deformation of the end 22 of the conveying tube 9 or of the valve member or connecting member 40, particularly, crimped inwardly, so as to form an axial abutment for the valve member 32.

In the finished conveying tube 9, the annular space 26 is preferably, evacuated and/or sealed in gastight manner. If necessary, the annular space 26 may also be filled with a filler material, plastics or the like (not shown).

The valve member or connecting member 40 or the connecting portion 35 preferably, has a length of less than 20%, in particular less than 10%, of the total length of the conveying tube 9. This makes production easier. The length of the conveying tube 9 or outer tube 24 is, preferably, at least 50 mm or 50 times the inner diameter.

The preferred multi-part construction of the conveying tube 9, is comprised, in particular, of more than two parts, preferably, three or four parts, may, if necessary, be implemented independently of the preferred double-walled construction of the conveying tube 9. The valve 10 is most preferably, formed by the valve member or connecting member 40 which is separately produced, but still fixedly connected to the conveying tube 9, and which forms, in particular, the receiving or valve region 31 for the valve member 32 of the valve 10.

Generally, it is pointed out that, in the proposed nebuliser 1, the container 3 can, preferably, be inserted, i.e., incorporated, in the nebuliser 1. Consequently, the container 3 is, preferably, a separate component. However, the container 3 or fluid chamber 4 may theoretically be formed directly by the nebuliser 1 or part of the nebuliser 1 or may otherwise be integrated in or attached to the nebuliser 1.

As already mentioned, individual features, aspects and/or principles of the embodiments described may also be combined with one another as desired and may be used particularly, in the known nebuliser according to FIGS. 1 & 2, but also in similar or different nebulisers.

Unlike freestanding equipment or the like, the proposed nebuliser 1 is preferably, designed to be portable, and in particular, is a mobile hand-operated device.

The proposed solution may, however, be used not only in the nebulisers 1 specifically described here but also in other nebulisers or inhalers, e.g., powder inhalers or so-called metered dose inhalers.

The nebuliser 1 is particularly, preferably, constructed as an inhaler, particularly, for medicinal aerosol treatment. Alternatively, however, the nebuliser, 1 may also be constructed for other purposes, preferably, for nebulising a cosmetic liquid, and in particular, as a perfume atomiser. Accordingly, the container 3 contains, for example, a pharmaceutical formulation or a cosmetic liquid, such as perfume or the like. Further, the proposed capillay can also be used in any kind of any dispensing device for the preferably, medical fluid 2. Thus, the term "nebuliser" is to be understood preferably, in such a broad sense.

Preferably, the fluid 2 is a liquid, as already mentioned, especially an aqueous or ethanol pharmaceutical formulation. However, it may also be some other pharmaceutical formulation, a suspension or the like, or particles or powder.

Preferred ingredients and/or formulations of the preferably, medicinal fluid 2 are listed hereinafter. As already stated, these may be aqueous or non-aqueous solutions, mixtures, formulations containing ethanol or solvent-free formulations or the like. It is particularly, preferable for the fluid 2 to contain:

As pharmaceutically active substances, substance formulations or substance mixtures, all invaluable compounds are used such as, for example, invaluable macromolecules as disclosed in EP 1 003 478. Preferably, substances, substance formulations or substance mixtures for treating respiratory complaints and administered by inhalation are used.

Particularly, preferred pharmaceutical compositions in this context are those which are selected from among the anticholinergics, betamimetics, steroids, phosphodiesterase IV inhibitors, LTD4 antagonists and EGFR kinase inhibitors, antiallergics, derivatives of ergot alkaloids, triptans, CGRP antagonists, phosphodiesterase V inhibitors, and combinations of such active substances, e.g., betamimetics plus anticholinergics or betamimetics plus antiallergics. In the case of combinations, preferably, at least one of the active substances comprises chemically bound water. Preferably, anticholinergic-containing active substances are used, as monopreparations or in the form of combined preparations.

The following are specifically mentioned as examples of the active ingredients or the salts thereof:

Anticholinergics which may be used are preferably, selected from among tiotropium bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobezilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenyl-propionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of the racemates, enantiomers or diastereomers thereof and optionally in the form of the solvates and/or hydrates thereof.

Betamimetics which may be used are preferably, selected from among albuterol, bambuterol, bitolterol, broxaterol, carbuterol, clenbuterol, fenoterol, formoterol, hexoprenaline, ibuterol, indacaterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzolsulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]-sulphonyl}ethyl]-amino}ethyl]-2(3H)-benzothiazolone, 1-(2-fluoro-4-hydroxy-phenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino) ethanol and 1-(4-ethoxycarbonyl-amino-3-cyano-5-fluorophenyl)-2-(tert.-butylamino)ethanol, optionally in the form of the racemates, enantiomers or diastereomers thereof and optionally in the form of the pharmacologically acceptable acid addition salts, solvates and/or hydrates thereof.

Steroids which may be used are preferably, selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate, (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate and etiprednol-dichloroacetate (BNP-166), optionally in the form of the racemates, enanitiomers or diastereomers thereof and optionally in the form of the salts and derivatives thereof, the solvates and/or hydrates thereof.

PDE IV-inhibitors which may be used are preferably, selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzamide, NCS-613, pumafentine, (−)p-[(4αR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene] acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, CI-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers thereof and optionally in the form of the pharmacologically acceptable acid addition salts, solvates and/or hydrates thereof.

LTD4-antagonists which may be used are preferably, selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methyl-ethyl)phenylpropyl)thio)methyl)cyclopropane-acetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-87107 and L-733321, optionally in the form of the racemates, enantiomers or diastereomers thereof, optionally in the form of the pharmacologically acceptable acid addition salts thereof and optionally in the form of the salts and derivatives thereof, the solvates and/or hydrates thereof.

EGFR-kinase inhibitors which may be used are preferably, selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

By acid addition salts, salts with pharmacologically acceptable acids which the compounds may possibly be capable of forming are meant, for example, salts selected from among the hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably, hydrochloride, hydrobromide, hydrosulphate, hydrophosphate, hydrofumarate and hydromethanesulphonate.

Examples of antiallergics are: disodium cromoglycate, nedocromil.

Examples of derivatives of the ergot alkaloids are: dihydroergotamine, ergotamine.

For inhalation, it is possible to use pharmaceutical compositions, pharmaceutical formulations and mixtures including the above-mentioned active substances, as well as the salts, esters and combinations of these active substances, salts and esters.

What is claimed is:

1. A nebuliser for a fluid comprising a conveying tube for conveying the fluid, wherein the conveying tube is constructed as a thick-walled capillary of a double-walled construction, wherein the conveying tube includes an inner tube and an outer tube, wherein a hollow annular space is formed between the inner tube and the outer tube, and wherein said hollow annular space is sealed in a gastight manner by a physical connection between the inner and outer tubes, at least one end of the inner tube being expanded substantially at least to the inner diameter of the outer tube, and further comprising an atomizing nozzle means for producing a spray of liquid particles that is located downstream of said conveying tube in a direction of fluid flow.

2. The nebuliser according to claim 1, wherein the inner tube and the outer tube extend concentrically with respect to one another.

3. The nebuliser according to claim 1, wherein the inner tube is connected to the outer tube by means of a radially widening connecting portion.

4. The nebuliser according to claim 3, wherein the inner tube is connected by means of at least one of welding and gluing.

5. The nebuliser according to claim 3, wherein the connecting portion is formed at one end of the inner tube.

6. The nebuliser according to claim 5, wherein the connecting portion is formed by means of molding at one end of the inner tube.

7. The nebuliser according to claim 3, wherein the connecting portion has an outer diameter which at least substantially corresponds to the inner diameter of the outer tube.

8. The nebuliser according to claim 3, wherein the connecting portion terminates flush with the end of the outer tube or set back therefrom.

9. The nebuliser according to claim 3, wherein an end of the tubes is connected by a spacer element of sleeve-shaped construction.

10. The nebuliser according to claim 9, wherein the spacer element has a wall thickness that amounts to at least 50% of the difference between the inner diameter of the outer tube and the outer diameter of the inner tube.

11. The nebuliser according to claim 3, wherein the length of the spacer element is less than 20% of the total length of the conveying tube.

12. The nebuliser according to claim 1, wherein the conveying tube comprises a plurality of parts.

13. The nebuliser according to claim 12, wherein the plurality of parts is formed by means of at least one of welding and adhesive bonding.

14. The nebuliser according to claim 1, wherein the conveying tube or at least part thereof is made of metal.

15. The nebuliser according to claim 1, wherein the conveying tube has a substantially smooth outer wall.

16. The nebuliser according to claim 1, wherein the conveying tube comprises an outer radial projection thereon.

17. The nebuliser according to claim 16, wherein the outer radial projection includes at least one of a flange having a crimped edge, and a radial indentation or recess.

18. The nebuliser according to claim 17, wherein the radial indentation or recess is formed by means of at least one of an annular groove, a depression and a bead.

19. The nebuliser according to claim 1, wherein the conveying tube has an outer diameter of 1 to 2 mm.

20. The nebuliser according to claim 1, wherein the length of the conveying tube is at least 50 mm.

21. The nebuliser according to claim 1, wherein the length of the conveying tube is at least 50 times the inner diameter of the conveying tube.

22. The nebuliser according to claim 1, wherein the conveying tube has an inner diameter of 0.1 to 0.6 mm.

23. The nebuliser according to claim 1, wherein the conveying tube has an outer diameter which is at least two times as large as the inner diameter.

24. The nebuliser according to claim 1, wherein the conveying tube performs a reciprocal movement during at least one of the removal of fluid, conveying of fluid, pressure generation and atomisation.

25. The nebuliser according to claim 1, wherein further comprising a container having a fluid chamber, which is opened by the attachment or insertion of the conveying tube.

26. The nebuliser according to claim 1, wherein the nebuliser is is adapted for use for medicinal treatment.

27. The nebuliser according to claim 26, wherein the nebuliser is an inhaler.

28. A nebuliser for a fluid comprising a conveying tube for conveying the fluid, wherein the conveying tube is constructed as a thick-walled capillary of a double-walled construction having an inner tube and an outer tube, wherein the space between the tubes is closed off at both ends by a physical connection between the tubes, the inner and outer tubes being rigidly connected together and wherein the conveying tube includes a valve for closing said inner and wherein the outer tube has an essentially cylindrical outer contour and at least one end of the inner tube is expanded substantially at least to the inner diameter of the outer tube, and further comprising an atomizing nozzle means for producing a spray of liquid particles that is located downstream of said conveying tube in a direction of fluid flow.

29. The nebuliser according to claim 28, wherein the valve is at one end of the conveying tube.

30. The nebuliser according to claim 28, wherein the conveying tube comprises the valve member or connecting member being separate and firmly connected to the conveying tube.

31. The nebuliser according to claim 30, wherein the conveying tube forms a receiving chamber or valve chamber for the valve member of the valve.

32. The nebuliser according to claim 28, wherein the inner tube is connected to the outer tube by means of a radially widening connecting portion.

33. The nebuliser according to claim 32, wherein the valve member or connecting member is mounted at the end of the conveying tube or at least one of the inner tube and outer tube.

34. The nebuliser according to claim 32, wherein the valve member or connecting member comprises a valve region having an external diameter which corresponds at least substantially to the external diameter of the outer tube or conveying tube.

35. The nebuliser according to claim 32, wherein the valve member or connecting member has a conical region.

36. The nebuliser according to claim 35, wherein the conical region forms a valve seat.

37. A nebuliser for a fluid comprising a movable conveying tube for conveying the fluid, wherein the conveying tube is constructed as a thick-walled capillary of a double-walled construction having an inner tube and an outer tube, the inner and outer tubes being rigidly connected together in a manner that the space between the tubes is closed off at both ends by a physical connection between the tubes, wherein the conveying tube is operable as a piston for pumping the fluid.

* * * * *